(12) United States Patent
Yang et al.

(10) Patent No.: US 6,872,386 B2
(45) Date of Patent: Mar. 29, 2005

(54) ORAL VACCINES

(75) Inventors: Huey-Lang Yang, Taipei (TW); James Chein-Chih Yu, Kaohsiung (TW); John Han-You Lin, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/946,273

(22) Filed: Sep. 5, 2001

(65) Prior Publication Data

US 2003/0044450 A1 Mar. 6, 2003

(51) Int. Cl.$^7$ .......................... A01N 63/00; A61K 47/00
(52) U.S. Cl. .................. 424/93.2; 424/93.1; 424/93.4; 424/93.51; 424/93.7; 424/410; 424/439; 424/442
(58) Field of Search .......................... 424/184.1, 204.1, 424/234.1, 265.1, 274.1, 93.1, 93.2, 93.3, 93.4, 93.6, 817, 827

(56) References Cited

U.S. PATENT DOCUMENTS 6,248,329 B1 * 6/2001 Chandrashekar et al.

OTHER PUBLICATIONS

Sano, Journal of Applied Ichthyology 14(3–4):131–137, Dec. 1998.*
Christie, Developments in Biological Standardization 90:191–199, 1997.*
Palm et al, International Symposium on Aquatic Animal Health, Program and Abstracts, W–24–1, 1994.*
Durbin et al, Journal of Aquatic Animal Health, 11(1):68–75, 1999.*
Yoichi et al. Vaccine, 19(4–5):579–588, 2000.*
Campbell et al, Fish & Shellfish Immunology 3(6):451–459 (abstract only), 1993.*
Speare et al, Journal of Fish Diseases, 21(2):93–100, 1998.*
Ellis, R.W. "Vaccines" Plotkin et al eds. Chapter 29, W.B. Saunders Co, Philadelphia PA, p. 571, 1988.*
*Oral vaccination of juvenile carp (Cyprinus carpio) and gilthead seabream (Sparus aurata) with bioencapsulated Vibrio anguillarum bacterin* by P.H.M. Joosten, M. Aviles–Trigueros, P. Sorgeloos, and J.H.W.M. Rombout. Fish & Shellfish Immunology, vol. 5, pp. 289–299, 1995.
*Bioencapsulation of Two Different Vibrio Species in Nauplii of the Brine Shrimp (Artemia franciscana)* by Bruno Gomez–Gil, Maria A. Herrera–Vega, F. Alberto Abreu–Brobois, and Ana Roque. Applied and Environmental Microbiology, Jun. 1998, pp. 2318–2322.
*Accumulation of Trimethoprim, sulfamethoxazole, and N–Acetylsufamethoxazole in Fish and Shrimp Fed Medicated Artemia franciscana* by M. Chair, J. H. Nelis, P. Leger, P. Sorgeloos, and A. P. De Leenheer. Antimicrobial Agents and Chemotherapy, Jul. 1996, pp. 1649–1652.
*Fish oral vaccine method combining bio–encapsulating and recombinant DNA technology* by Chien–Chih Yu, John Han–You Lin, Carmen Lopez and J. P. R. Rajan of Institute of Bioagricultural Sciences—Academia Sinica, Taiwan and Huey–Lang Yang of Institute of Biotechnology—National Chen Kung University, Taiwan.
Campbell et al., "Uptake of *Vibrio anguillarum* vaccine by *Artemia salina* as a Potential Oral Delivery System to Fish Fry" Fish & Shellfish Immunology 3:451–459, 1993.
Christie, K.E., "Immunization with Viral Antigens: Infectious Pancreatic Necrosis" Dev. Biol. Stand. 90:191–199, 1997.
Durbin et al., "Immunization against Furunculosis in Rainbow Trout with Iron–Regulated Outer Membrane Protein Vaccines: . . . " J. of Aquatic Animal Health 11:68–75, 1999.
Ellis, R. W., "New Technologies for Making Vaccines" In Vaccines. Philadelphia: WB Saunders Company, pp. 568–575, 1998.
Yoichi Matsunaga et al., "Oral Immunization with Size–Purified Microsphere Beads as a Vehicle Selectively Induces Systemic Tolerance and Sensitization" Vaccine 19:579–588, 2001.
Palm et al., "Specific Humoral Response of Rainbow Trout to Injection, Immersion, and Oral Immunization Against *Vibrio anguillarum*" International Symposium on Aquatic Animal Health: Program and Abstracts, pp. W–24.1 (see abstract), 1994.
Sano, T., "Control of Fish Disease, and the Use of Drugs and Vaccines in Japan" J. Appl. Ichthyol. 14:131–137, 1998.
Speare et al., "Induced Resistance in Rainbow Trout, *Oncorhynchus mykiss* (Walbaum), to Gill Disease Associated with the . . . " J. of Fish Diseases 21:93–100, 1998.

* cited by examiner

*Primary Examiner*—Patricia A. Duffy
(74) *Attorney, Agent, or Firm*—Fish & Richardson P.C.

(57) ABSTRACT

This invention features an oral vaccine that includes a multiple-cell organism for use as food for an aquatic animal to be vaccinated, and a single-cell organism fed to, and as a result, bioencapsulated by, the multiple-cell organism. The single-cell organism has been transformed to express a recombinant antigen that induces an immune response in the aquatic animal and thereby vaccinates the aquatic animal (e.g., a fish or a shrimp).

4 Claims, No Drawings

ORAL VACCINES

BACKGROUND

There is a need for an efficacious immunization of aquatic animals. For example, infectious diseases are common on fish farms, due to intensive fish farming that facilitates the transmission of pathogens in an aqueous environment. Dunn et al. (1990) *Aquaculture Engineering* 9: 23-3. Preventing aquatic animal diseases by oral vaccination has several advantages over other methods: It is non-stressful, requires little labor, and can be applied at a large scale. However, many oral vaccines have been found ineffective as a result of failure to uptake sufficient dosage of antigen, poor antigen delivery and antigen degradation in the digestive tract.

SUMMARY

This invention relates to a novel oral vaccine useful for immunizing an aquatic animal (e.g., a fish or a shrimp), against an infectious disease (e.g., a bacterial, viral, or parasitic disease).

In one aspect, the present invention features an oral vaccine that includes a multiple-cell organism for use as food for an aquatic animal to be vaccinated, and a single-cell organism fed to, and as a result, bioencapsulated by, the multiple-cell organism. The single-cell organism has been transformed to express a recombinant antigen that can induce an immune response in the aquatic animal and thereby vaccinate the aquatic animal. The term "food" as used herein refers to food (e.g., bait) itself or a food additive. More specifically, the single-cell organism contains a heterologous nucleic acid encoding an amino acid sequence of an antigen of interest. The nucleic acid is in a recombinant vector, which also includes one or more regulatory sequences (e.g., promoters or enhancers) operatively linked to the nucleic acid to be expressed. The antigen need not be the wild-type amino acid sequence found in a naturally occurring gene, as long as it is capable of inducing an immune response. For example, a fish oral vaccine includes artemia (the multiple-cell organism) that has fed on, and encapsulates *Escherichia coli* (the single cell organism), which has been transformed to express a bacterial antigen.

In another aspect, the present invention features a method for preparing an oral vaccine. The method includes (1) providing a single-cell organism which has been transformed to express a recombinant antigen that can induce an immune response in an aquatic animal and thereby vaccinate the aquatic animal, and (2) feeding the single-cell organism to a multiple-cell organism. As a result of the feeding, the multiple-cell organism (e.g., artemia, rotifer, algae, a paramecium, or an oyster embryo) bioencapsulats the single-cell organism (e.g., a bacterium or yeast). Such a multiple-cell organism can be fed to an aquatic animal as an oral vaccine. Also within the scope of this invention is a method for orally delivering a vaccine to an aquatic animal by feeding an oral vaccine described above to the animal to be vaccinated.

Other features, objects, and advantages of the invention will be apparent from the description and from the claims.

DETAILED DESCRIPTION

The present invention relates to an oral vaccine for immunization of an aquatic animal against infectious diseases, either for prophylactic vaccination or for therapeutic vaccination. The oral vaccine includes a multiple-cell organism that has fed on, and therefore contains, a single-cell organism. The single-cell organism fed to the multiple-cell organism has been transformed to express a recombinant antigen that can induce an immune response in the aquatic animal. The just-described multiple-cell organism, fed to the aquatic animal, serves as an oral vaccine to the animal. In other words, an antigen, being expressed in a single-cell, multiple-cell organism or in a aquatic animal, is delivered to the aquatic animal via two steps of feeding, i.e., the above-described single-cell organism fed to the multiple-cell organism, and the multiple-cell organism from previous step fed to the aquatic animal. As a result of the delivery, the antigen can induce an immune response in the animal.

What antigen to be expressed of course depends on whether the induced immune response is against a targeted pathogen. Having the identified antigen that triggers the immune response, one can clone it into a recombinant vector that includes a nucleic acid encoding the antigen and one or more regulatory sequences operatively linked to the nucleic acid. The regulatory sequences can be those that direct constitutive expression of the antigen, as well as inducible sequences. The recombinant vector can be designed based on such factors as the single-cell organism to be transformed by it. It may contain more than one nucleic acid encoding different antigens. For example, a recombinant vector contains nucleic acids encoding two antigens, which can induce immune responses against the same or different pathogens. Alternatively, the recombinant vector may contain a nucleic acid encoding a polypeptide (e.g., a helper epitope) that is not antigenic, but itself or its encoded peptide serves to enhance an immune response against a targeted pathogen.

The just-described recombinant vector is introduced into a suitable single-cell organism via conventional transformation or transfection techniques, including a variety of art-recognized techniques for introducing a foreign nucleic acid (e.g., DNA) into a suitable host single-cell organism, e.g., calcium phosphate or calcium chloride co-precipitation, DEAE-dextran-mediated transfection, lipofection, or electroporation. Examples of suitable single-cell organisms are described, for example, in Goeddel (1990) *Gene Expression Technology: Methods in Enzymology* 185, Academic Press, San Diego, Calif. One or more just-described single-cell organisms are then fed to a suitable multiple-cell organism, a food or food additive to an aquatic animal to be vaccinated. Accordingly, the just-obtained multiple-cell organism serves as an oral vaccine, in which an antigen is in the single-cell organism that is bioencapsulated by the multiple-cell organism. Unexpectedly, such an oral vaccine has been found effective due to difficult antigen degradation in the digestive tract of the aquatic animal.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE

Materials and Methods

Animals. Zebra fish, *Danio rerio*, were used. Zebra fish were kept at a suitable temperature such as 28.5° C., and reared in re-circulated, filtered water. At the start of each experiment, fish were 50 days old. Until vaccination, fish were fed with regular brine shrimp (*artemia* nauplii). After vaccination, feeding with pelleted dry food commenced amounting to 5% of fish body weight per day.

Plasmid construction and antigen preparation. *Pseudomonas aeruginosa* (PE toxin) is a bacterium that causes nosocomial infections, and has a $LD_{50}$ value (lethal dose fifty) of 1 μg for a mouse. Also recombinant Pseudomonas exotoxin A (PE) can elicit effective protection against native PE toxin challenge in an animal model.

Plasmid pJH4, which encodes a PE gene without a signal peptide and a c-terminal terminus, was a gift from Dr. Hwang (Hwang et al. (1987) *Cell.* 48: 129–136). The PE gene was isolated from pJH4 by digestion with EcoR I and Hind III, and the isolated PE gene was inserted into another plasmid pET24a with the same restriction enzyme cohesive ends (EcoR I and Hind III), thereby producing the plasmid pET24a-PE. The resulting plasmid was transformed into *E. coli* strain BL21 (DE3). The bacteria containing the plasmid were cultured at 37° C. in LB broth with kanamycine at a concentration of 50 μg/mL. When absorbance at 600 nm reached 0.6, isopropyl-1-thio-β-D-galactoside was added to a final concentration of 1 mM. After 150 min, the bacteria were harvested, washed twice with phosphate-buffered saline (PBS), and thus, PE-enriched *E. coli* was obtained. The bacteria were kept at −20° C. until fed to *artemia*, and the expressed PE protein was analyzed by using SDS-PAGE.

PE-enriched artemia nauplii preparation. *Artemia* nauplii were hatched in fresh seawater at 29±1° C., under continuous light and sufficient air. 40 hr after hatch, *artemia* were collected and fed with PE-enriched *E. coli* (or *E. coli* control). After feeding, *artemia* nauplii were collected, and washed five times with PBS. *Artemia* nauplii were fed to zebra fish immediately, or kept at −20° C. for subsequent use or analysis.

SDS-PAGE electrophoresis and western blotting. The PE protein in an *artemia* sample was analyzed by using Protein Assay Kit (BIO-RAD, 2000 Alfred Nobel Drive, Hercules, Calif. 94547, USA). The sample was homogenized in Laemmli buffer (Laemmli, U.K. (1970) *Nature (London)* 227: 650–685), and boiled for 5 minutes. The PE protein was analyzed by 8% polyacrylamide gels containing SDS (SDS-PAGE), and stained with Coomassie blue after electrophoresis. It was more than 40% in the total *E. coli*-expressed proteins. In an immunoblotting assay, the PE protein in the sample was electrophoresed on gels, transferred to a nitrocellulose paper; incubated with the rabbit anti-PE antibody and a second antibody (goat anti-rabbit conjugated with alkaline phosphatase), and then stained with an alkaline phosphatase substrate (BIO-RAD). Procedures were carried out under conditions recommended by the supplier (BIO-RAD). The anti-PE antibody was generated in rabbits by immunization. 250 μg of the PE protein emulsified in Freund's complete adjuvant was administered to the rabbits. The pooled rabbit-anti-PE antibody fractions were prepared for western blotting analysis.

Vaccination schedule. PE-enriched artemia nauplii were fed to zebra fish that have been starved for 24 hours before vaccination. During feeding, the water flow was stopped. Fish were fed four times a day. Control fish (non-vaccinated fish) were fed with control *artemia* nauplii. After 6 weeks, both vaccinated and non-vaccinated fish were fed with pelleted dry food. After 3 weeks, fish were challenged with a PE toxin (Sigma)

Challenge test with PE toxin. In order to determine $LD_{50}$ values of PE in zebra fish, five experimental groups (six non-vaccinated fish each) were tested. Five groups were starved for 24 hours, anaesthetized by using 200 ppm of 2-phenoxyethanol, and intraperitonally injected with 0, 0.5, 1, 1.5 and 2 μg of the PE toxin, respectively. A $LD_{50}$ value of PE for zebra fish was thus determined at the range of 1–1.2 μg in 50 days old zebra fish. In a subsequent experiment, vaccinated fish were challenged with 1.2 μg of the PE toxin.

Immunohistochemistry study of uptake of PE infish. After feeding with the enriched artemia nauplii, six groups (three fish each) were killed at the time 0, 1, 2, 3, 6, and 12 hours, respectively, and put on ice for 1 minute. Fish was dissected, fixed in 4% formalin overnight, and after rinsing with PBS and dehydration, embedded in paraffin wax. Continuous sections were cut, mounted on poly-L-lysine treated slides, and incubated with a 3% $H_2O_2$-containing PBS solution to inactivate endogenous peroxidase. The slides were then rinsed with PBS-E (PBS with 1 mM EDTA and dehydrated with 50% (v/v, 50% ethanol and 50% water) and 90% ethanol (v/v, 90% ethanol and 10% water). The PE protein was detected by an immunoperoxidase reaction using rabbit-anti-PE serum (1:1000) and a goat-anti-rabbit horseradish peroxidase (HRP) conjugate (1:200). Conjugates were visualized with a HRP substrate (0.012% v/v hydrogen peroxide in water) and chromogen (0.4 mg/mL). After aminoethylcarbazole was applied to the sections for 15 minutes, the slides were washed twice with PBS-E. The sections was counterstained with acid hematoxylin for 5 minutes, blued with aqueous ammonia for 1 min, and then rinsed with PBS. Detection was carried out by using water as mounting medium, and slides were viewed under a microscope at a magnification of 40–400×. Tissues containing the recombinant PE were stained as reddish-brown color.

Results

Determination of $LD_{50}$. Since the weight of zebra fish varies even at same age, the $LD_{50}$ value of the PE toxin for 50 days old zebra fish was determined to be between 1 to 1.2 μg and $LD_{50}$ dose of 1.2 μg per fish was used as the challenge dose. To confirm the $LD_{50}$, twenty-one non-vaccinated fish were challenged by intraperitonal injections. Ten fish (50%) died within a week, within this group, 7 fish (33%) died between 2 to 3 days. Further, more than 80% of fish had symptoms of hemorrhage, as observed on fish skin and adipose tissues. All of the fish had lost appetite for a period up to 7 to 10 days after the injections. However, control fish, intraperitonally injected with PBS, had no symptoms of hemorrhage and lost appetite for only one day.

The efficacy of an oral vaccine. Sixteen fish vaccinated by feeding oral vaccine were challenged by intraperitonal injections of 1.2 μg PE toxin. Four vaccinated fish (mortality rate is 25%) died within 5 days. For comparison, among the six fish in the non-vaccinated group (mock vaccination groups with artemia fed with regular *E. coli*), four fish died within 5 days (mortality rate is 75%). The results show that the oral vaccine containing the recombinant *E. coli* bioencapsulated by artemia is efficacious. Further, the vaccinated fish also lost appetite, but they recovered 2 to 3 days earlier than those fish survived from PE challenge in the non-vaccinated group.

The optimal time of preparation enriched artemia nauplii. To evaluated the optimal time of prepare enriched *artemia*, the *E. coli* (BL21, DE3) that expressed PE protein was fed to *artemia* nauplii. The *artemia* nauplii were killed at time 0, 15, 30, 45, 60, 90, and 120 minutes after feeding, and washed five times with PBS to eliminate the superficially attached *E. coil*. The artemia nauplii samples were suspended in 6 M urea and sonicated. The PE protein extracted from the samples were analyzed by SDS-PAGE and detected by western blotting analysis with rabbit-anti-PE antibody (see above). The results show that the amount of the PE protein in artemia nauplii increases after feeding, reaches a plateau after 30 to 60 minutes, and drops later on. Accordingly, the optimal time for feeding artemia nauplii in this exampled experiment is 45 minutes.

Comparison of recombinant and bacterial native antigens. Six strains of *Pseudomonas aeruginosa* (ATCC 15693, ATCC 29260, ATCC 33449, ATCC 33354, ATCC 33355 and ATCC 33359) that conferred PE toxin and PE-enriched *E. coli* recombinant were individually fed to *artemia* nauplii. PE proteins extracted from seven *artemia* nauplii samples were analyzed by SDS-PAGE and detected by western blotting analysis with rabbit-anti-PE antibody (see above). *Artemia* fed with PE-enriched *E. coli* recombinant contained PE protein that can be easily observed by the PAGE gel analysis but those *artemia* fed with six strains of *Pseudomonas aeruginosa* did not show any PE protein detectable in PAGE gel analysis. The results indicated that the feeding of recombinant *E. coli* with specific antigen did increase the amount of antigen as compared to the prior art that fed *artemia* with intact bacterial pathogen. See Gomez-Gil et al. (1998) *Appl Environ Microbiol* 64: 2318–2322. Thus, fish can easily get sufficient PE protein to trigger an immune response after uptake of an oral vaccine containing the recombinant PE-enriched *E. coli* bioencapsulated by *artemia* nauplii.

The uptake of the PE protein in fish intestine. Histological observation aided by immuno-assay with anti-PE antibody indicated that in a period of one to three hours after feeding with *artemia* nauplii, the PE protein was observed in the lumen of the fish intestine, and the uptake reached the maximal amount in two hours after feeding. Data show that particles of the PE protein were found to pass the mucosal and enter the epithelial cell. The particles began to disappear after six hours, and totally disappeared after 12 hours.

The safety evaluation of the oral vaccine of this invention. No abnormality was observed in the morphology, appetite, swimming behavior, or death in all fish fed with the oral vaccine.

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, an oral vaccine as described above is used for immunization of domestic animals or humans. Thus, other embodiments are also within the claims.

What is claimed is:

1. An oral vaccine, comprising:

an *artermia* for use as food for a fish; and a single-cell organism fed to, and bioencapsulated by, the *artemia*;

wherein the single-cell organism is transformed to express a recombinant antigen of Pseudomonas exotoxin A that induces an immune response in the fish.

2. The oral vaccine of claim 1, wherein the single-cell organism is a bacterium or yeast.

3. The oral vaccine of claim 2, wherein the single-cell organism is a bacterium.

4. The oral vaccine of claim 3, wherein the single-cell organism is *Escherichia coli*.

* * * * *